United States Patent [19]

Fisher

[11] Patent Number: 4,894,396

[45] Date of Patent: Jan. 16, 1990

[54] IMPRESSION MATERIAL

[75] Inventor: Robert G. Fisher, Beckenham, England

[73] Assignee: ESPE Stiftung & Co. Produktions- und Vertriebs-KG, Seefeld, Fed. Rep. of Germany

[21] Appl. No.: 211,122

[22] Filed: Jun. 21, 1988

Related U.S. Application Data

[63] Continuation of Ser. No. 40,806, Apr. 21, 1987, abandoned.

[30] Foreign Application Priority Data

Apr. 23, 1986 [GB] United Kingdom ................. 8609851

[51] Int. Cl.$^4$ ........................... A61K 6/10; A61C 9/00
[52] U.S. Cl. .................................... 523/109; 433/214; 524/906
[58] Field of Search ..................... 523/109; 433/214; 524/906

[56] References Cited

U.S. PATENT DOCUMENTS

| | | | |
|---|---|---|---|
| 2,567,979 | 9/1951 | Taylor | 523/109 |
| 3,558,540 | 1/1971 | Molnar | 523/109 |
| 3,850,870 | 11/1974 | Kawakami et al. | 523/109 |
| 4,341,716 | 7/1982 | Diery et al. | |
| 4,493,911 | 1/1985 | Schmitt et al. | |
| 4,672,081 | 6/1987 | Fisher et al. | 523/109 |

FOREIGN PATENT DOCUMENTS

| | | | |
|---|---|---|---|
| 0861002 | 1/1971 | Canada | 523/109 |
| 2027035A | 2/1980 | United Kingdom | |

Primary Examiner—Herbert J. Lilling
Attorney, Agent, or Firm—Birch, Stewart, Kolasch & Birch

[57] ABSTRACT

A two part impression material comprising a first part comprising a product of the reaction of an alpha, beta-ethylenically unsaturated dicarboxylic acid anhydride and a liquid polydiene resin and a second part comprising a setting agent for the reaction product which setting agent is an alkoxylated fatty monoamine or an alkoxylated fatty polyamine having from 2 to 30 moles of alkoxylate per mole of the fatty amine, the alkoxylate groups being one or more alkoxylates selected from the group comprising ethoxylate, propoxylate and butoxylate, the first part and/or the second part also comprising an organic liquid which is incompatible with both the setting agent and the reaction product. A method of taking a dental impression using the reaction product of the first and second parts of the two part dental impression material is also disclosed.

11 Claims, No Drawings

IMPRESSION MATERIAL

This is a continuation of co-pending application Ser. No. 07/040,806, filed on Apr. 21, 1987, now abandoned.

The present invention relates to a two part impression material, suitable for use as a dental impression material, to a method of preparing the impression material and to a process for using the two part impression material to obtain an impression.

British Patent GB 2,027,035B discloses a two-part dental impression material comprising a first part containing a product of the reaction of an alpha, beta ethylenically unsaturated dicarboxylic acid anhydride and a liquid polydiene resin and a second part containing a setting agent which has at least two reactive hydrogen atoms per molecule and is capable of forming a crosslink between molecules of said reaction product. The patent states that suitable setting agents include amines, polyols, amides, alkanolamines and alkanolamides. Also included are polyepoxides in combination with an epoxide ring-opening or carboxylic anhydride ring-opening compound.

European Patent Application 0149354 discloses a two part impression material, suitable fo use as a dental impression material, comprising a first part containing a product of the reaction of an alpha, beta-ethylenically unsaturated dicarboxylic acid anhydride and a liquid polydiene resin and a second part containing a setting agent for the said reaction product in which the setting agent is an alkoxylated fatty monoamine or an alkoxylated fatty polyamine having from 2 to 30 moles of alkoxylate per mole of the fatty amine, the alkoxylate groups being one or more alkoxylates selected from the group comprising ethoxylate, propoxylate and butoxylate groups.

It has now been found that the inclusion of certain organic liquids in composition of the kind disclosed in EP-A-0149354 improves the handleability of the compositions and in particular reduces tackiness to skin.

Thus according to the present invention a two part impression material comprising a first part comprising a product of the reaction of an alpha, beta-ethylenically unsaturated dicarboxylic acid anhydride and a liquid polydiene resin and a second part comprising a setting agent for the said reaction product which setting agent is an alkoxylated fatty monoamine or an alkoxylated fatty polyamine having from 2 to 30 moles of alkoxylate per mole of the fatty amine, the alkoxylate groups being one or more alkyloxylates selected from the group comprising ethoxylate, propoxylate and butoxylate groups is characterised in that the first part and/or the second part also comprises an organic liquid which is incompatible with both the setting agent and the reaction product of the alpha, beta-ethylenically unsaturated dicarboxylic acid anhydride and liquid polydiene resin. The term "incompatible" when used in this context means that the organic liquid is substantially insoluble in and substantially unreactive with the reaction product and the setting agent such that, when blended into the first part and/or the second part of the impression material, it forms a relatively stable emulsion in which the organic liquid is the dispersed phase and the reaction product or the setting agent is the continuous phase.

The organic liquids are preferably non-polar. The organic liquids suitable for use in the present invention are preferably liquid at 10° C., more preferably they are liquid at $-5°$ C. and most preferably they remain liquid at $-10°$ C. Suitable organic liquids include, for example, liquid hydrocarbons, liquid polymers and mixtures thereof.

The liquid hydrocarbons may be any hydrocarbons acyclic or cyclic, saturated or unsaturated which satisfy the requirements of being a liquid which is incompatible with the reaction product and setting agent. Preferably, the hydrocarbon has a boiling point greater than 100° C. Liquid paraffin or kerosene are suitable liquid hydrocarbons for use in the present invention.

The liquid polymers suitable for use in the present invention include for example, polyolefins. Preferably, the liquid polymer does not contain —OH groups or reactive nitrogen groups, e.g. amino groups. The polymer may have any molecular weight provided that it is liquid and incompatible with the reaction product and setting agent. Typically, the number average molecular weight will be less than 10,000. The viscosity of the liquid polymer is preferably not more than 170 Poise at 15° C. Particularly suitable organic polymers have been found to be liquid polybutadiene and liquid polyisobutene.

Increasing the amount of organic liquid tends to reduce the tackiness of the impression material i.e. the combined weight of the first and second parts. Preferably, the organic liquid comprises not more than 30% by weight of the total weight of the impression material.

Although the organic liquid may be included in either the first part or the second part of the two-part impression material according to the present invention it is preferably blended with the reaction product of the alpha, beta-ethylenically unsaturated dicarboxylic acid anhydride and liquid polyidene resin of the first part. However, the organic liquid may tend to separate from the said reaction product and form a separate layer if the first part comprises more than 45 parts by weight of the organic liquid per 55 parts by weight of the reaction product. It may therefore be necessary to have a proportion of the organic liquid in the first part of the impression material and a proportion in the second part. The inclusion of a compound to assist or improve the stabilisation of the of the emulsion may allow larger amounts of organic liquid to be included in the first part or second part of the impression material than would otherwise be the case. For example, a compound such as polyisobutene succinic anhydride or a maleinised polybutadiene having a relatively low degree of maleinisation can be used to stabilise an emulsion of polybutadiene in a maleinised polybutadiene having a higher degree of maleinisation.

Although the two part impression material according to the present invention is particularly suitable for use as a dental impression material, it may be used in other applications. For example, the two part impression material may be used, to take an impression of an ear for use in the fitting of hearing aids. Thus, although the invention will be described hereinafter with particular reference to its use as a dental impression matrial this should not be taken as limiting the invention to this application.

The present invention includes a method of preparing an impression material, particularly a dental impression material, which method comprises mixing together the two parts of the impression material as described above and also includes the product of the reaction between the first and second part of the impression material.

The invention also includes a method of taking a dental impression which comprises placing in a dental impression mould a dental impression material prepared by mixing together the two parts of the impression material as hereinbefore described, bringing the mould into contact with the patient's teeth or jaws or with a dental model or prosthesis, allowing the dental impression material to set and thereafter removing the mould to leave an impression in the dental impression material. In addition to reducing tackiness to skin, impression materials according to the present invention may also have a reduced tendency to adhere to teeth and may allow impressions to be taken of wet teeth. Most commercially available elastomeric dental impression materials generally require the teeth to be dried prior to taking an impression.

Alkoxylated monoamines and polyamines are known and some are commercially available. They may be prepared by alkoxylating fattyamines by known methods. The fatty amines are preferably derived from a C8 to C22 compound containing one or more saturated or unsaturated fatty acid. More preferably, the fatty amines are derived from C12 to C18 compounds such as, for example, oleic, lauric, palmitic or stearic acid, tallow or hydrogenated tallow, coconut oil or soya bean oil. The alkoxylate groups are preferably ethoxylate or propoxylate groups or mixtures thereof. Preferably the setting agents have from 5 to 15 moles of alkoxylate per mole of fatty amine.

Setting agents suitable for use in the compositions according to the present invention include alkoxylated fatty amines having the following general formula:

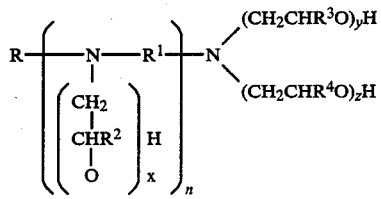

where
R is a hydrocarbyl group having from 8 to 22 carbon atoms
$R^1$ is a $(CH_2)_3$ or $CH_2CH(CH_3)CH_2$
$R^2$, $R^3$ and $R^4$ are the same or different and are H, $CH_3$ or $CH_2CH_3$
n is 0 or a positive integer from 1 to 3
x, y and z are the same or different and are individually zero or a positive integer from 1 to 6, the sum of x, y and z being from 2 to 30, preferably 5 to 15.

If x, y or z in the above formula is greater than 1, then the alkoxylate group may be a mixture of alkoxylates. For example, if y=3 then $(CH_2CHR^3)_y$ may comprise two ethoxylate groups and one propoxylate group.

The extent of alkoxylation is the number of moles of alkoxylate per mole of fatty amine i.e. in the above formula, the extent of alkoxylation of a monoamine is y+z and of a diamine is x+y+z. However, in practice an alkoxylated fatty amine is likely to be a mixture of amines. Thus, although x, y and z are given as integers or zero in the above formula, the extent of alkoxylation may not be an integer.

Suitable setting agents for use in the present invention include;

N,N-bis($11^1$-hydroxy-$3^1$:$6^1$:$9^1$-trioxaundecyl)-octadec-9-enylamine

N,$N^1$,$N^1$-tris($11^1$-hydroxy-$2^1$,$5^1$,$8^1$-trimethyl-$3^1$:$6^1$:$9^1$-trioxadodecyl)N-ocetadec-9''-enyl-1,3-diaminopropane N,$N^1$,$N^1$-tris($8^1$-hydroxy-$2^1$,$5^1$-dimethyl-$3^1$:$6^1$-dioxanonyl) N-octadec-$9^{11}$-enyl-1,3-diaminopropane.

The most suitable alpha, beta-ethylenically unsaturated dicarboxylic acid anhydride for use in the preparation of the reaction product is maleic anhydride.

The liquid polydiene resin may be a homopolymer of a conjugated diene or a copolymer of a conjugated diene and one or more copolymerisable ethylenically unsaturated monomer. If the liquid polydiene resin is a copolymer, it preferably comprises at least 50% by weight of a conjugated diene. The polydiene resin may be prepared by known polymerisation methods.

The conjugated diene is preferably butadiene and an example of a suitable copolymersiable ethylenically unsaturated monomer is styrene.

The number average molecular weight of the liquid polydiene resin is preferably from 1,000 to 10,000.

The reaction of a liquid polydiene, such as polybutadiene, and an alpha, beta-ethylenically unsaturated dicarboxylic acid anhydride, such as maleic anhydride, is well known. A conventional method of preparing maleinised polydiene is disclosed in British Patent GB 2,027,035B. The reaction between the liquid polydiene and the alpha-beta-ethylenically unsaturated dicarboxylic acid will be referred to as "functionalisation" in this specification and the reaction product will be referred to as "functionalised" polymer. Typically, the extent of functionalisation, e.g. the amount of maleic anhydrie units associated with the polydiene, is from 5 to 20 parts by weight per 100 parts of the polydiene.

After functionalisation, the reaction product can be stripped by heating under vacuum to remove any traces of volatile material. A volatile solvent or diluent can be added to the functionalised polymer prior to the stripping step. The functionalised polymer can also be washed with a solvent with which it is immiscible, e.g. water, in order to remove soluble material. The final product preferably has a free maleic anhydride content of not more than 0.15% by weight.

Generally the first and/or second parts of the impression material according to the present invention contain fillers, plasticisers and other additives and are in the form of a paste. Conveniently both parts of the impression material are in the form of pastes, the viscosity of the pastes being such that the two parts may be easily mixed together. Mixing of the two parts is generally effected by hand using a spatula or similar tool. The two parts may be pigmented such that they have contrasting colours. This provides a means of visually indicating when a homogeneous mix is achieved.

The use of fillers in the first and/or second part of the impression material affects the viscosity of the part prior to mixing and confers the properties of opacity and/or toughness on the final impression material. The inclusion of fillers may also affect the rate of setting of the materials. As already mentioned, the viscosity of each part of the impression material should be such that the two parts may be easily mixed together and so the amount of filler used will be determined to some extent by the viscosities of the other components. Typically, the proportion of filler in either or both parts of the impression material is from 0 to 80% by weight and is conveniently from 10 to 70% by weight. The water content of the filler is preferably relatively low e.g. less than 0.1% by weight. A relatively high water content may adversely affect the storage stability of the product.

Suitable fillers include those conventionally used in dental impression materials such as for example whiting, china clay, ground limestone, barytes, talc and silica.

Conventional pigments and dyes, e.g. those known for use in dental materials, may be used to colour one or both parts of the impression material.

Diluents and plasticisers such as those conventionally used in polymer compositions may be included in either or both parts of the impression material.

One or both parts of the impression material may also contain a mould release agent such as, for example, silicone oil or polyethylene glycol.

The relative proportions of the first and second parts which are mixed together to form the impression material depend on a number of factors such as, the amount of the setting agent in the second part and the amount of the functionalised polymer and its extent of functionalisation, the setting time required and the degree of cross-linking required. The relative proportions are generally selected such that there are at least sufficient active groups in the second part of the impression material containing the setting agent to react with all of the anhydride groups of the functionalised polymer in the first part. Preferably, however, the proportions are such that the amount of setting agent used is at least 1.5 times the stoichiometric amount required to react with all of the anhydride groups of the functionalised polymer. A practical upper limit is 4 times the stoichiometric amount. More preferably the amount of setting agent is from 1.75 to 2.25 times the stoichiometric amount required to react with all of the anhydride groups of the functionalised polymer. The use of more than the stoichiometric amount of setting agent improves the tension set of the final impression material.

The invention is illustrated by the following examples:

EXAMPLE 1

A two part dental impression material according to the present invention was prepared by mixing together the following components to form a first part and a second part:

|  | Parts by Weight |
|---|---|
| First Part | |
| Maleinised polybutadiene | 97.5 |
| Titanium dioxide | 2.5 |
| Second Part | |
| Alkoxylated fatty amine | 13.7 |
| Filler | 56.8 |
| Liquid paraffin heavy BP | 13.1 |
| Polyethylene glycol | 1.8 |
| Polybutadiene | 14.2 |
| Dye | 0.5 |

The maleinised polybutadiene used was a reaction product of maleic anhydride and liquid polybutadiene sold by Revertex Limited under the designation LITHENE LX16 10MA (LITHENE is a trademark). The molecular weight of the polybutadiene was approximately 8000 and the polymer contained 10 parts by weight of maleic anhydride per 100 parts by weight of polybutadiene.

The alkoxylated fatty amine setting agent used in the second part of the composition was a propoxylated oleyl diamino propane. The extent of propoxylation i.e. the number of moles of propoxylate per mole of oleyl diaminopropane was $9.0 \pm 0.4$.

The filler used was precipitated calcium carbonate coated with 3% by weight of stearate sold by Witco Chemicals under the designation CALOFORT S (CALOFORT is a trademark).

The polyethylene glycol was a commercially available material sold by BP Chemicals under the trademark BREOX which had a molecular weight of 200.

The polybutadiene was supplied by Revertex Limited under the designation LITHENE $N_4$ 5000 and had a molecular weight of approximately 5000.

The dye used to colour the second part of the impression material as an oil soluble dye, Red Lake No. 30.

The first part and second part were mixed together with a spatula in the weight ratio of 1:3.6. Aproximately one minute from the start of mixing the material was smeared over the palm of a hand and also squeezed between the finger tips. Between 3 and 6 minutes from the start of mixing the set material could be relatively easily peeled from the skin.

EXAMPLE 2

Example 1 was repeated except that the proportions of the components of the second part of the impression material were as follows:

| Second Part | Parts by Weight |
|---|---|
| Alkoxylated fatty amine | 12.6 |
| Filler | 52.3 |
| Liquid Paraffin | 12.0 |
| Polyethylene glycol | 1.6 |
| Polybutadiene | 21.0 |
| Dye | 0.5 |

The first part and second part were mixed together with a spatula in the weight ratio of 1:4.1. Once again the material was relatively easily removed from skin.

A sample of the mixture of the first part and second part was placed in an open-ended cylinder and, before the composition set, the open end of the cylinder was pressed against the palm of a hand so that the exposed composition was pressed on to the skin for about 3 minutes. The force required to pull the cylinder from the skin was then measured. The test was repeated several times and the force required was found to be in the range 65 to 80 $gcm^{-2}$. For comparison, the test was repeated using (A) a similar composition which contained no polybutadiene or liquid paraffin and (B) a commercially available polyethyleneimine dental impression material. The force required to remove the cylinder containing either of the comparative materials was at least 25% greater than the force required to remove the cylinder when it contained the impression material of Example 2. It was also noted that the material according to the present invention did not adhere to rubber gloves as much as did the commercial dental impression material.

EXAMPLE 3

An emulsion comprising 25% by weight of polybutadiene in 75% by weight of maleinised polybutadiene was prepared using a domestic food mixer. The polybutadiene and maleinised polybutadiene were the same as used in Example 1. This emulsion was mixed with a second part in the weight of ratio of 1:0:2.6, the second part comprised the following components:

| Second Part | Amount (parts by weight) |
| --- | --- |
| Alkoxylated fatty amine | 15.9 |
| Liquid paraffin heavy BP | 15.2 |
| Polyethylene glycol | 2.05 |
| Red Lake No 30 | 0.8 |
| Filler | 66.1 |

The mixture was applied to the skin over the palm of a hand and between the fingers. After allowing the composition to set, it was relatively easily peeled from the skin.

The mixed composition had the following physical properties:

| Setting time | 2 minutes |
| --- | --- |
| Tension Set | 2.0% |
| Elongation at break | 270% |
| International Rubber Hardness (30 mins) | 38 |

The properties were determined according to BS 4269: Part 1 1968 except for the International Rubber Hardness which was determined according to ASTM D 1415-68.

EXAMPLE 4

A two part dental impression material was prepared by mixing together the following components to form a first part and a second part:

| | Amount |
| --- | --- |
| First Part | |
| Maleinised polybutadiene | 97.5 |
| Titanium dioxide | 2.5 |
| Second Part | |
| Alkoxylated fatty amine | 12.6 |
| Filler | 52.3 |
| Liquid paraffin heavy BP | 12.0 |
| Polyethylene glycol | 1.6 |
| Polyisobutene | 21.0 |
| Dye | 0.5 |

The polyisobutene used is a commercially available low molecular weight polyisobutene sold by BP Chemicals Limited under the trade designation HYVIS 07 (HYVIS is a trade mark). The titanium dioxide used was micronised titanium dioxide. The other components were as used in Example 1. The first part and second part were mixed together with a spatula in the weight ratio of 1:4.1. The material was spread over the palm and fingers of a hand as in the previous Examples. The set material could be relatively easily peeled from the skin.

EXAMPLE 5

A two part dental impression material was prepared by mixing together the following component to form a first part and a second part:

| | Amount (parts by weight) |
| --- | --- |
| First part | |
| Maleinised polybutadiene | 68.29 |
| Polybutadiene | 29.27 |
| Polyethylene fibers | 1.95 |
| Titanium dioxide | 0.49 |
| Second part | |
| Alkoxylated fatty amine | 15.82 |

-continued

| | Amount (parts by weight) |
| --- | --- |
| Liquid paraffin heavy BP | 14.03 |
| Filler | 60.83 |
| Polyethylene glycol | 1.95 |
| Dye | 0.48 |
| Polybutadiene | 6.89 |

The maleinised polybutadiene, alkoxylated fatty amine setting agent, filler, polyethylene glycol, polybutadiene, liquid paraffin and dye were all the same as used in Example 1.

The first part and second part were mixed together with a spatula in the weight ratio of 1:2.3.

The mixture was applied to dried teeth within 2 minutes of the start of mixing using a commerical dental tray. After 5 minutes from the start of mixing the tray containing the set material was easily removed from the teeth. The process was repeated except that the teeth were not dried prior to taking the impression. In both cases sharp, clear impression were obtained.

The mixed composition had the following physical properties:

| Setting time | 130 seconds |
| --- | --- |
| Tension set | 2.5% |
| Elongation at break | 200% |
| International Rubber Hardness (30 mins) | 35 |

The properties were determined according to BS 4269: Part 1 1968 except for the International Rubber Hardness which was determined according to ASTM D 1415-68.

The mixed composition was applied over the fingers of fifty people. After allowing the composition to set, it was easily removed from the skin.

I claim:

1. A two part impression material comprising a first part comprising a product of the reaction of an alpha, beta-ethylenically unsaturated dicarboxylic acid anhydride and a liquid polydiene resin and a second part comprising a setting agent for the reaction product which setting agent is an alkoxylated fatty monoamine or an alkoxylated fatty polyamine having from 2 to 30 moles of alkoxylate per mole of the fatty amine, the alkoxylate groups being one or more alkoxylates selected from the group comprising ethoxylate, propoxylate and butoxylate, the impression material being characterized in that the first part and/or the second part also comprises an organic liquid which, when blended into the first part and/or second part of the impression material, forms a relatively stable emulsion in which the organic liquid is the dispersed phase and the reaction product or the setting agent is the continuous phase.

2. An impression material as claimed in claim 1 in which the organic liquid is non-polar.

3. An impression material as claimed in claim 2 in which the organic liquid is one or more liquid hydrocarbons, one or more liquid polymers or a mixture of liquid hydrocarbons and liquid polymers.

4. An impression material as claimed in claim 3 in which the organic liquid is selected from the group comprising liquid paraffin, kerosene, polybutadiene, polyisobutene, or a mixture thereof.

5. An impression material as claimed in claim 1 in which the reaction product is maleinised polybutadiene.

6. A method of preparing an impression material comprising mixing together the first part and the second part of a two part impression material as claimed in claim 1 and allowing them to react together.

7. An impression material comprising the product of the reaction between the first part and the second part of a two part impression material as claimed in claim 1.

8. An impression material as claimed in claim 7 comprising (a) maleinised polybutadiene, (b) an alkoxylated fatty monoamine or an alkoxylated fatty polyamine, (c) liquid paraffin, (d) polyethylene glycol and (e) polybutadiene or polyisobutene.

9. An impression material as claimed in claim 1, in which the organic liquid is polyisobutene polybutadiene, kerosene, or a mixture thereof.

10. An impression material as claimed in claim 1, in which the organic liquid is polyisobutene, polybutadiene, or a mixture thereof.

11. An impression material as claimed in claim 1, in which the organic liquid is a mixture of (a) liquid paraffin and (b) polybutadiene or polyisobutene.

* * * * *